(12) United States Patent
Cawley et al.

(10) Patent No.: US 9,119,673 B2
(45) Date of Patent: Sep. 1, 2015

(54) SPINAL CORRECTION SYSTEM WITH MULTI-STAGE LOCKING MECHANISM

(75) Inventors: Trace R. Cawley, Boca Raton, FL (US); John R. Pepper, Cheshire, CT (US); Doris Blake, Delray Beach, FL (US)

(73) Assignee: US Spine, Inc., Salt Lake City, UT (US)

( * ) Notice: Subject to any disclaimer, the term of this patent is extended or adjusted under 35 U.S.C. 154(b) by 717 days.

(21) Appl. No.: 12/876,975

(22) Filed: Sep. 7, 2010

(65) Prior Publication Data

US 2010/0331888 A1    Dec. 30, 2010

Related U.S. Application Data

(63) Continuation of application No. 11/455,419, filed on Jun. 19, 2006.

(60) Provisional application No. 60/691,708, filed on Jun. 17, 2005.

(51) Int. Cl.
*A61B 17/70*    (2006.01)

(52) U.S. Cl.
CPC ......... *A61B 17/7032* (2013.01); *A61B 17/7037* (2013.01); *A61B 17/7035* (2013.01)

(58) Field of Classification Search
CPC ........... A61B 17/7001; A61B 17/7032; A61B 17/7035; A61B 17/7037; A61B 17/7038; A61B 17/7046
USPC ............. 606/53, 60, 264–277, 300–320, 322, 606/323, 324–328
See application file for complete search history.

(56) References Cited

U.S. PATENT DOCUMENTS

| | | | | |
|---|---|---|---|---|
| 5,672,176 A | * | 9/1997 | Biedermann et al. | 606/271 |
| 5,690,630 A | * | 11/1997 | Errico et al. | 606/264 |
| 6,565,565 B1 | * | 5/2003 | Yuan et al. | 606/272 |
| 6,755,829 B1 | * | 6/2004 | Bono et al. | 606/308 |
| 6,786,903 B2 | * | 9/2004 | Lin | 606/23 |
| 2002/0116001 A1 | * | 8/2002 | Schafer et al. | 606/61 |
| 2003/0187439 A1 | * | 10/2003 | Biedermann et al. | 606/61 |
| 2004/0030337 A1 | * | 2/2004 | Alleyne et al. | 606/61 |
| 2005/0080415 A1 | * | 4/2005 | Keyer et al. | 606/61 |
| 2005/0228385 A1 | * | 10/2005 | Iott et al. | 606/61 |

(Continued)

FOREIGN PATENT DOCUMENTS

WO    WO 2004089245 A2 * 10/2004

*Primary Examiner* — Pedro Philogene
*Assistant Examiner* — Lynnsy Summitt
(74) *Attorney, Agent, or Firm* — Phillips Ryther & Winchester; Matthew D. Thayne

(57) ABSTRACT

In a rod fixation system of the type used to treat various spinal conditions, the same fastener is used to lock both a polyaxial screw and a rod in position. A spinal correction device according to the invention, adapted for use with a rod and a polyaxial screw having a ball-shaped head and a threaded end, comprises a head-body and a cap. The head-body includes a lower internal cavity to receive the ball-shaped head of the screw, an upper bore to receive a fixation rod therethrough, and an upper end configured to receive the cap. The head-body and the cap are configured such that a first rotation of the cap locks the polyaxial screw in position, and a second rotation of the cap locks the rod in position. In the preferred embodiment, the head-body includes one or more gaps to facilitate flexion of the head-body as a rotational torque is placed on the cap. The gap or gaps may be horizontal, vertical or other angles relative to the axis of the entrapped rod.

18 Claims, 5 Drawing Sheets

(56) References Cited

U.S. PATENT DOCUMENTS

| | | | |
|---|---|---|---|
| 2005/0267472 A1* | 12/2005 | Biedermann et al. | 606/61 |
| 2006/0149241 A1* | 7/2006 | Richelsoph et al. | 606/61 |
| 2006/0161153 A1* | 7/2006 | Hawkes et al. | 606/61 |
| 2006/0173456 A1* | 8/2006 | Hawkes et al. | 606/61 |

* cited by examiner

SPINAL CORRECTION SYSTEM WITH MULTI-STAGE LOCKING MECHANISM

REFERENCE TO RELATED APPLICATIONS

This application is a continuation of U.S. patent application Ser. No. 11/455,419, filed Jun. 19, 2006, which claims priority from U.S. Provisional Patent Application Ser. No. 60/691,708, filed Jun. 17, 2005, the entire content of which is incorporated herein by reference.

FIELD OF THE INVENTION

This invention relates generally to spinal correction and, in particular, to a system incorporating a multi-stage locking mechanism.

BACKGROUND OF THE INVENTION

There are many spine-related conditions, such as scoliosis, which require multi-level correction/fixation. Numerous plate and rod systems are available for this purpose, many of which have received patent protection. One of the deficiencies with existing systems, however, is that the mechanism used to lock the polyaxial screw is different from the mechanism used to lock the rod, thereby requiring additional parts and less manageable installation steps.

SUMMARY OF THE INVENTION

Broadly, this invention resides in a rod fixation system to treat various spinal conditions, wherein the same fastener is used to lock both a polyaxial screw and a rod in position. A spinal correction device according to the invention, adapted for use with a rod and a polyaxial screw having a ball-shaped head and a threaded end, comprises a head-body and a cap. The head-body includes a lower internal cavity to receive the ball-shaped head of the screw, an upper bore to receive a fixation rod therethrough, and an upper end configured to receive the cap. The head-body and the cap are configured such that a first rotation of the cap locks the polyaxial screw in position, and a second rotation of the cap locks the rod in position.

In the preferred embodiment, the head-body includes one or more gaps to facilitate flexion of the head-body as a rotational torque is placed on the cap. The gap or gaps may be horizontal, vertical or other angles relative to the axis of the entrapped rod. With appropriate selection of materials and cross-section, sufficient "flexion" may be established without the need for gaps.

Tapered threads may be used on the head-body and/or cap to achieve subsequent tightening of the polyaxial screw and rod to a continuous rotational movement. An optional compression-enhancing bushing may be disposed between the rod and the ball-shaped head of the screw. Although the invention is described in conjunction with rod fixation, extensions to rod and plate or plate-only configurations are possible.

DETAILED DESCRIPTION OF THE INVENTION

Broadly, this invention resides in a rod fixation system to treat various spinal conditions, wherein the same fastener is used to lock both a polyaxial screw and a rod in position. Although the invention is described in conjunction with rod fixation, extensions to rod and plate or plate-only configurations are possible.

Figure 1:
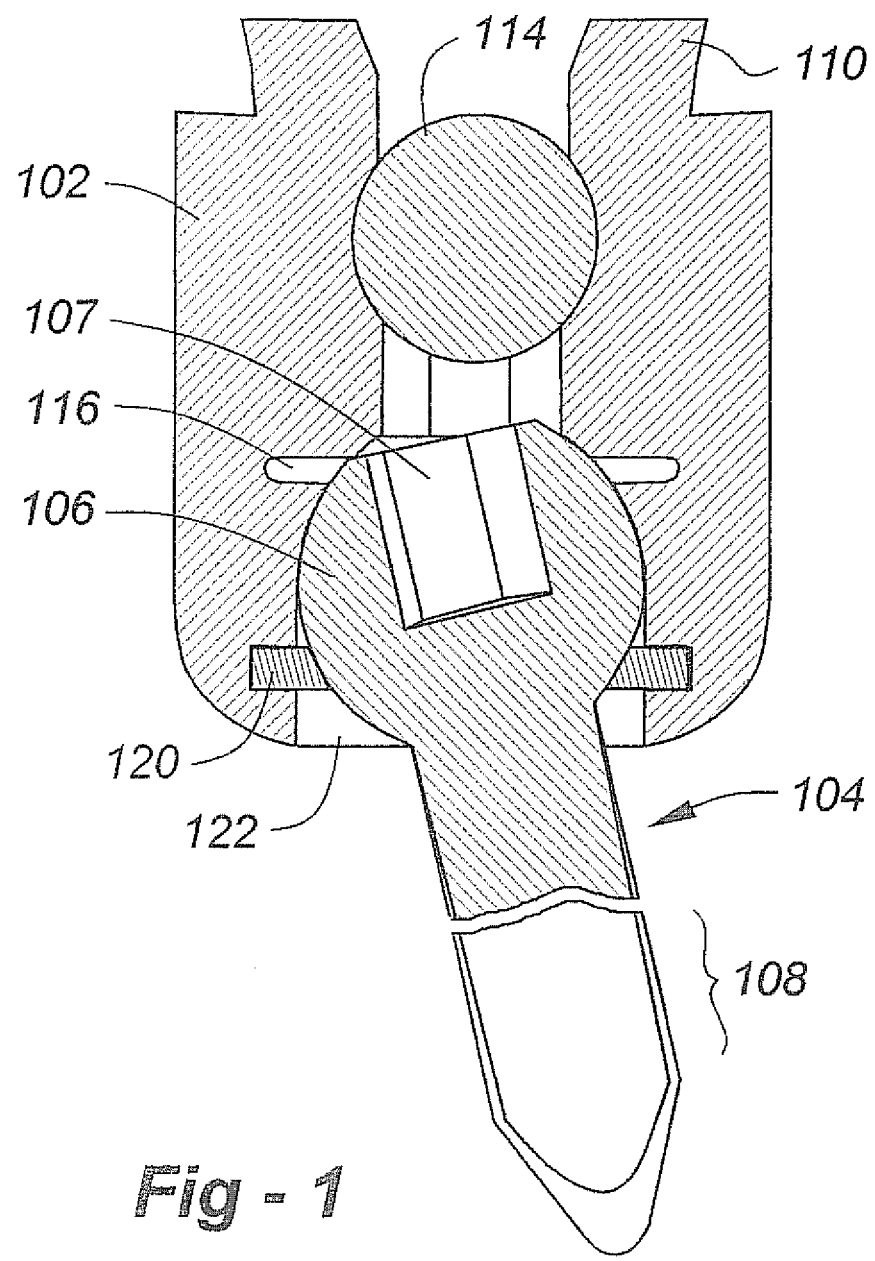
FIG. 1 is a drawing that shows a cross-section of a preferred embodiment of the invention.
Figure 2:
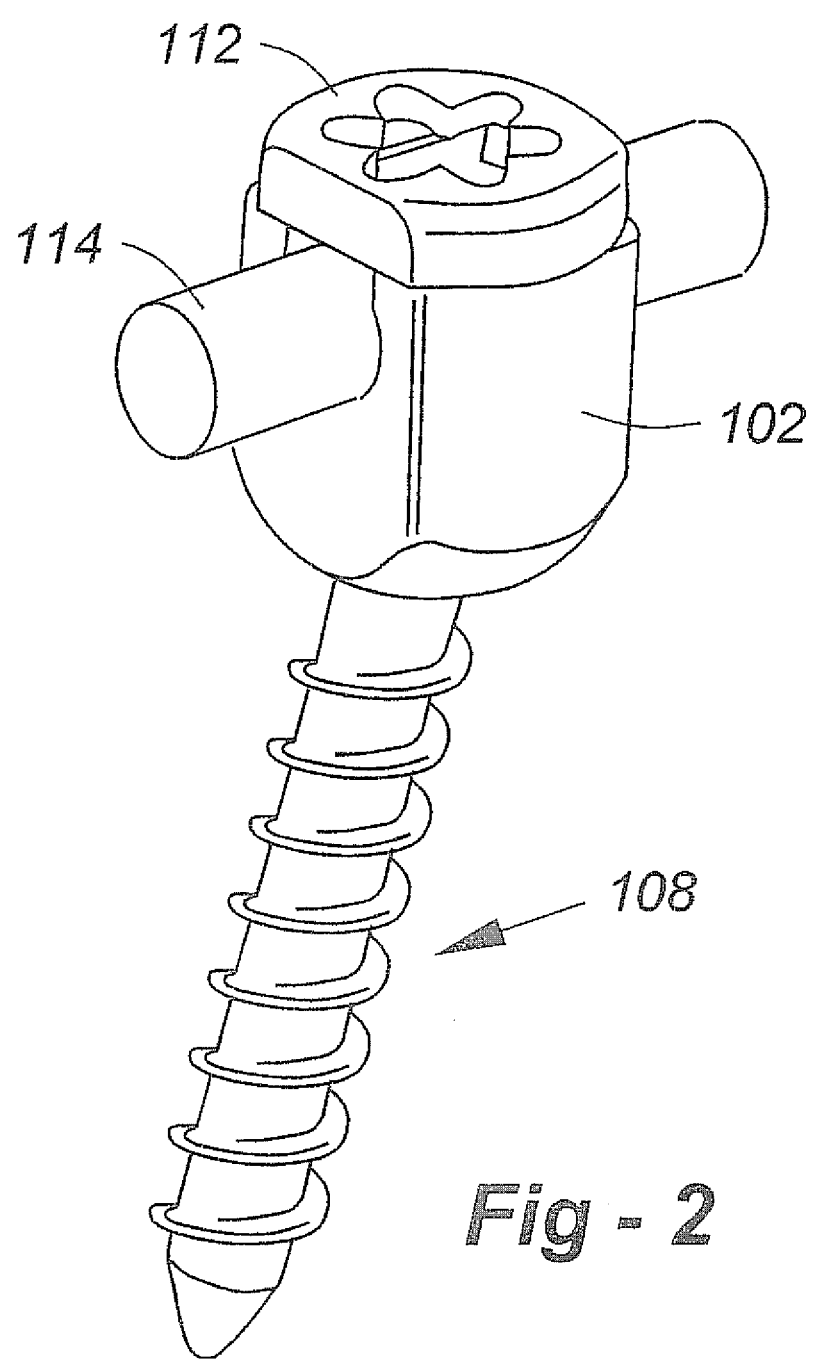
FIG. 2 is an oblique view of the embodiment of FIG. 1.

Reference is now made to FIGS. 1 and 2, which show from a cross-section and oblique view, respectively, a first preferred embodiment of the invention utilizing three primary components, namely, a head-body 102, a polyaxial screw 104, and a cap 112 (not shown in FIG. 1). The polyaxial screw 104 includes a proximal hemispherical head 106 and a distal threaded portion 108. The ball portion of the screw includes some type of turning aperture, such as hex depression 107. The screw 104 is held in position within the head-body 102 through bushing 120 and fastener 122, facilitating assembly from the bottom. The fastener 122 may be threaded, press fit or otherwise secured in position.

Above the hemispherical portion 106 of the polyaxial screw 104, is a partially cylindrical passage to receive a rod 114. Note the gap 116 formed within the head-body 102 internally to the head-body, and around the upper portion of the spherical head 106 of screw 104.

Broadly according to the invention, when cap 112 is placed onto the head-body 102, a first rotation of the cap 112 locks the polyaxial screw in position, while allowing the rod a slight degree of movement. However, with further rotational force applied to the cap 112, the rod is then locked in position, forming a rigid, unified structure. The polyaxial screw is screwed into position using a hex driver 107 with the screw 104 aligned the head-body 102, after which time the hex driver is removed, allowing the head-body to swivel and the rod 114 to be placed through the head-body.

Figure 3:
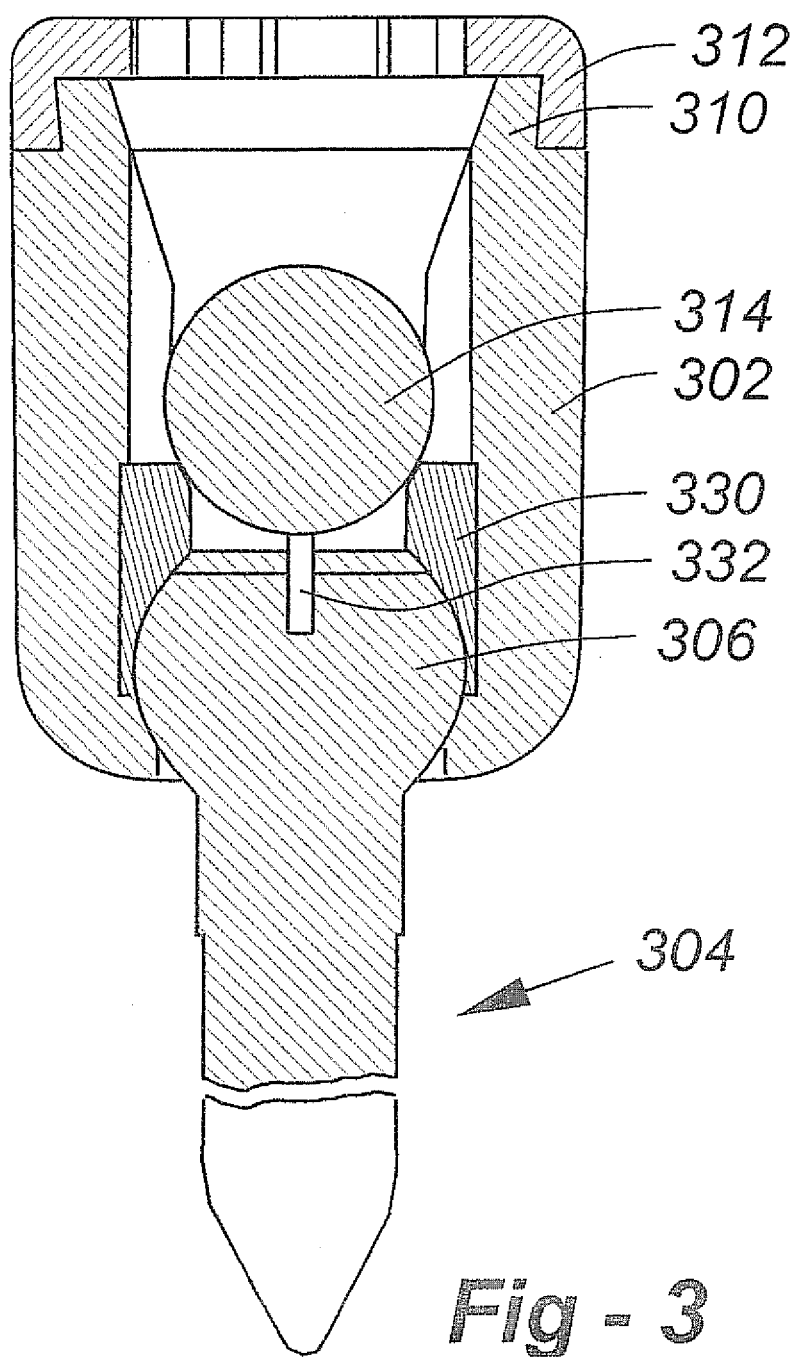
FIG. 3 is a drawing that shows a cross-section of an alternative embodiment of the invention.
Figure 4:
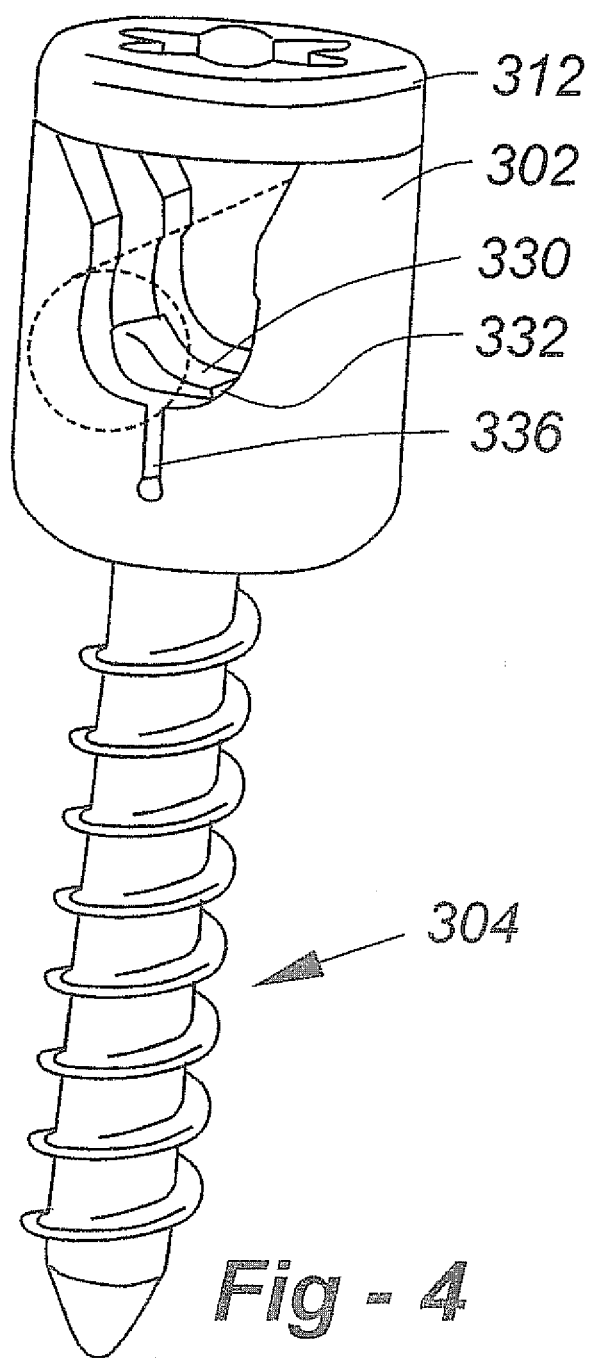
FIG. 4 is an oblique view of the embodiment of FIG. 3.

FIGS. 3 and 4 illustrate an alternative embodiment of the invention, utilizing four basic components, namely, those shown in FIGS. 1 and 2 with slight variation, and further including a bushing 330 having a slot 332 which aligns with a slot 336 formed through head-body 302. Polyaxial screw is shown at 304, having a proximal at least semi-spherical head 306. The rod 314 is shown in phantom.

The head-body 302 includes an upper portion 310 adapted to receive cap 312 as discussed previously. The operation of the alternative embodiment of FIGS. 3 and 4 is essentially the same as that of FIGS. 1 and 2, namely, that through a first rotational torque on cap 312, the polyaxial screw 304 is held in relative angular position with respect to head-body 302, such that with a subsequent torque applied to cap 312, rod 314 is locked in position. The purpose of bushing 330 is to provide additional compressive strength without the need for as much rotational torque as might be required in the preferred embodiment of FIGS. 1 and 2.

Figure 5A:
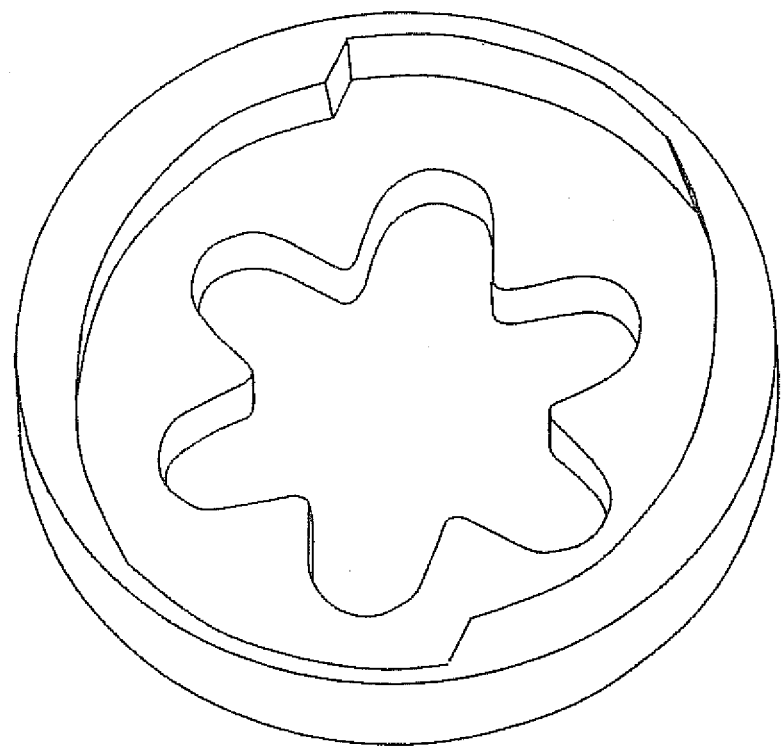
FIG. 5A is a bottom-up drawing of caps 112, 312.
Figure 5B:
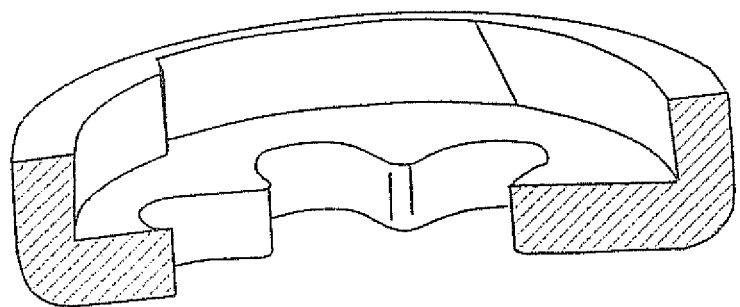
FIG. 5B is an oblique, partial cross-sectional view of caps 112, 312.
Figure 5C:
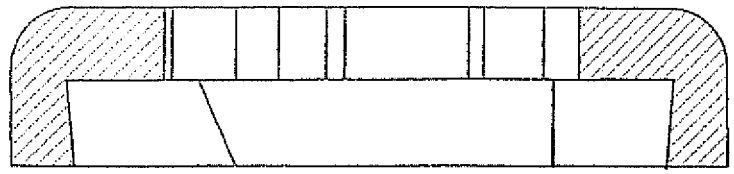
FIG. 5C is a side cross sectional view of caps 112, 312.

FIG. 5A is a bottom-up drawing of caps 112, 312. FIG. 5B is an oblique, partial cross-sectional view of caps 112, 312, and FIG. 5C is a side cross section. Note that due to the geometries involved, a first rotational torque through a predetermined angle, such as 90 degrees, causes the polyaxial screw to be locked in position, and that a subsequent rotational torque of an additional one-quarter turn of the rod to be locked in position.

Those of skill in the art will appreciate that as an alternative to a geometric relationship of the type just described, tapered threads may be used on the head-body and/or cap to achieve subsequent tightening of the polyaxial screw and rod to a continuous rotational movement. Additionally, although gaps are shown in the head-body as being horizontal and vertical, mixtures of these and angles other than horizontal and vertical may be used and, indeed, with appropriate selection of materials and cross-section, sufficient "flexion" may be established without the need for gaps. In terms of materials, the assemblies described may be formed from any bio-compatible sufficiently strong materials, such as chrome, cobalt or other alloys, ceramics or combinations thereof.

We claim:

1. A spinal correction device adapted for use with a rod and a polyaxial screw having a ball-shaped head and a threaded end, the device comprising:
   a head-body and a cap, the head-body having a lower internal cavity to receive the ball-shaped head of the screw, an upper bore to receive a fixation rod therethrough, and an upper end configured to receive the unthreaded cap, wherein the cap comprises a cap rim, wherein the head-body comprises a head-body rim, and wherein the cap rim is configured to mate with and engage the head-body rim, wherein the cap rim varies in thickness around at least a portion of the perimeter of the cap, wherein the cap rim comprises at least one tapering section in which the cap rim thickness gradually varies;
   wherein the head-body and the unthreaded cap are configured such that:
      a first rotation of the unthreaded cap locks the polyaxial screw in position, and
      a second rotation of the unthreaded cap locks the rod in position.

2. The device of claim 1, wherein the head-body includes one or more gaps to facilitate flexion of the head-body as a rotational torque is placed on the cap.

3. The device of claim 1, further comprising a compression-enhancing bushing disposed between the rod and the ball-shaped head of the screw.

4. The device of claim 1, wherein the cap rim comprises at least one ledge that is positioned to transition between at least one tapering section and at least one substantially non-tapering section.

5. The device of claim 4, wherein the ledge is defined by an abrupt increase in the thickness of the cap rim from an end of the substantially non-tapering section to transition to an end of the tapering section.

6. The device of claim 1, wherein, when the cap is engaged with the head-body, the cap rim is angled relative to a longitudinal axis of the head-body.

7. The device of claim 6, wherein, when the cap is engaged with the head-body, the head-body rim is angled relative to the longitudinal axis of the head-body in a complementary manner such that the head-body rim mates with the cap rim.

8. The device of claim 1, wherein the tapering section is configured such that the cap rim increases in thickness from a first end of the tapering section to a second end of the tapering section.

9. The device of claim 1, wherein the cap rim further comprises at least one section that is at least substantially non-tapering.

10. The device of claim 9, wherein the at least one section that is at least substantially non-tapering in a direction perpendicular to a circumference of the cap.

11. A spinal correction device adapted for use with a fixation rod, comprising:
   a polyaxial screw having a ball-shaped head and a threaded end;
   a head-body and an unthreaded cap, the head-body having a lower internal cavity to receive the ball-shaped head of the screw, an upper bore to receive the fixation rod therethrough, and an upper end configured to receive the unthreaded cap, wherein the cap comprises a cap rim, wherein the head-body comprises a head-body rim, and wherein the cap rim is configured to mate with and engage the head-body rim, wherein the cap rim varies in thickness around at least a portion of the perimeter of the cap, wherein the cap rim comprises at least one tapering section in which the cap rim thickness gradually varies; and
   wherein the head-body and the cap are configured such that:
      a first rotation of the unthreaded cap locks the polyaxial screw in position, and
      a second rotation of the unthreaded cap locks the rod in position.

12. The device of claim 11, wherein the head-body includes one or more gaps to facilitate flexion of the head-body as a rotational torque is placed on the cap.

13. The device of claim 11, further comprising a compression-enhancing bushing disposed between the rod and the ball-shaped head of the screw.

14. The device of claim 11, wherein the cap rim further comprises at least one substantially non-tapering in which the cap rim thickness is at least substantially constant, and wherein the thickness of the substantially non-tapering section is less than the thickness of at least a portion of the tapering section.

15. A spinal correction system, comprising:
   a fixation rod;
   a polyaxial screw having a ball-shaped head and a threaded end;
   a head-body and a cap, the head-body having a lower internal cavity to receive the ball-shaped head of the screw, an upper bore to receive the fixation rod therethrough, and an upper end configured to receive the cap, wherein the cap is configured to engage the head-body via a non-threaded connection, wherein the cap comprises a cap rim, wherein the head-body comprises a head-body rim, and wherein the cap rim is configured to mate with and engage the head-body rim, wherein the cap rim varies in thickness around at least a portion of the perimeter of the cap, wherein the cap rim comprises at least one tapering section in which the cap rim thickness gradually varies around at least a portion of the perimeter of the cap, and wherein the cap comprises an unthreaded cap; and
   wherein the head-body and the cap are configured such that:
      a first rotation of the cap locks the polyaxial screw in position, and
      a second rotation of the cap locks the rod in position.

16. The system of claim 15, wherein the head-body includes one or more gaps to facilitate flexion of the head-body as a rotational torque is placed on the cap.

17. The system of claim 15, further comprising a compression-enhancing bushing disposed between the rod and the ball-shaped head of the screw.

18. The system of claim 15, wherein the cap rim further comprises at least one section that is at least substantially non-tapering.

* * * * *